United States Patent
Knauf et al.

(10) Patent No.: US 9,896,407 B2
(45) Date of Patent: Feb. 20, 2018

(54) EXHAUST GAS CLEANING IN A METHOD FOR CONTINUOUSLY PRODUCING DINITROTOLUENE

(71) Applicant: Covestro Deutschland AG, Leverkusen (DE)

(72) Inventors: Thomas Knauf, Dormagen (DE); Jürgen Münnig, Kaarst (DE); Wolfgang Lorenz, Dormagen (DE); Bernd Pennemann, Bergisch Gladbach (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/514,107

(22) PCT Filed: Sep. 29, 2015

(86) PCT No.: PCT/EP2015/072397
§ 371 (c)(1),
(2) Date: Mar. 24, 2017

(87) PCT Pub. No.: WO2016/050759
PCT Pub. Date: Apr. 7, 2016

(65) Prior Publication Data
US 2017/0291869 A1 Oct. 12, 2017

(30) Foreign Application Priority Data
Oct. 2, 2014 (EP) .................................. 14187532

(51) Int. Cl.
C07C 201/08 (2006.01)
C07C 201/16 (2006.01)
C07C 205/06 (2006.01)
B01D 53/00 (2006.01)

(52) U.S. Cl.
CPC .......... *C07C 201/08* (2013.01); *B01D 53/002* (2013.01); *C07C 201/16* (2013.01); *B01D 2257/7027* (2013.01)

(58) Field of Classification Search
CPC ... C07C 201/08; C07C 201/16; C07C 205/06; B01D 53/002; B01D 2257/7027
See application file for complete search history.

(56) References Cited

U.S. PATENT DOCUMENTS

| | | |
|---|---|---|
| 4,663,490 A | 5/1987 | Gerken et al. |
| 5,275,701 A | 1/1994 | Mazzafro et al. |
| 5,313,009 A | 5/1994 | Guenkel et al. |
| 5,963,878 A | 10/1999 | Brereton et al. |
| 9,227,909 B2 | 1/2016 | Knauf et al. |
| 2004/0262238 A1 | 12/2004 | Munnig et al. |
| 2008/0086017 A1 | 4/2008 | Pohl et al. |
| 2012/0228218 A1 | 9/2012 | Fritz et al. |
| 2015/0175522 A1 | 6/2015 | Knauf et al. |

FOREIGN PATENT DOCUMENTS

DE 19636191 A1 2/1998

OTHER PUBLICATIONS

Hermann et al; "Industrial Nitration of Toluene to Dinitrotoluene Requirements of a Modem Facility for the Production of Dinitrotoluene"; Chapter 21; ed. L.F. Albright, R.V. C Carr, R.J. Schmitt; American Chemical Society 1996; ACS Symposium Series: Washington, DC.
Ullmann'S Encyklopadie der technischen Chemie; 4th edition, vol. 17, pp. 391-417, 1979, Verlag Chemie Weinheim / New York.
Billet, Reinhard; "Verdampfung und ihre technischen Anwendungen"; Verlag Chemie Weinheim—Deerfield Beach, Florida—Basel; 1981, chapter 4.1.2, pp. 208-230.

*Primary Examiner* — Jafar Parsa
(74) *Attorney, Agent, or Firm* — Donald R. Palladino

(57) ABSTRACT

The invention relates to a method for producing dinitrotoluene, comprising the following steps: a) nitrating toluene with a mixture of nitric acid and sulfuric acid and subsequently separating a sulfuric-acid-containing aqueous phase that arises in the nitration, wherein a raw dinitrotoluene is obtained, b) washing the raw dinitrotoluene in a water wash with neutral and/or alkaline washing water, wherein a pre-cleaned dinitrotoluene, which contains at least water in addition to dinitrotoluene, is obtained after the washing water used in the last wash has been separated, and c) separating the water from the pre-cleaned dinitrotoluene, d) collecting the waste water from steps a), b), and/or c), e) optionally extracting the collected waste water from step d) with toluene and returning the thus obtained organic phase to step a), f) freeing the collected waste water from step d), or, if the optional step e) is performed, the extracted waste water from step e), of toluene in a toluene stripper, wherein a toluene-containing exhaust gas flow is obtained, g) feeding at least one exhaust gas flow from steps a), b), c), d), e), or f) into an exhaust gas condenser and removing the toluene contained in the at least one exhaust gas flow in said exhaust gas condenser, wherein the method comprises the following further step: h) feeding the exhaust gas flow arising in step g) after the condensing out of the toluene to a thermal exhaust air cleaning, wherein nitrogen is added to the exhaust gas flow to be fed to the exhaust gas condenser or to the exhaust gas flow leaving the exhaust gas condenser, wherein preferably a nitrogen concentration in the exhaust gas flow of at least 0.1 vol % is set, especially preferably of at least 0.5 vol %.

15 Claims, No Drawings

EXHAUST GAS CLEANING IN A METHOD FOR CONTINUOUSLY PRODUCING DINITROTOLUENE

CROSS-REFERENCE TO RELATED APPLICATIONS

This application is a national stage application under 35 U.S.C. § 371 of PCT/EP2015/072397, filed Sep. 29, 2015, which claims the benefit of European Application No. 14187532.8, filed Oct. 2, 2014, both of which being incorporated by reference herein.

FIELD

The present invention relates to a process for producing dinitrotoluene, comprising the steps of:
a) nitration of toluene with a mixture of nitric acid and sulfuric acid with subsequent separation of a sulfuric-acid-containing aqueous phase formed during the nitration to obtain a crude dinitrotoluene,
b) washing the crude dinitrotoluene in a water wash with neutral and/or alkaline washing water, wherein after separation of the washing water employed in the last wash a prepurified dinitrotoluene is obtained which comprises not only dinitrotoluene but also at least water and
c) separating the water from the prepurified dinitrotoluene,
d) collecting the wastewaters from steps a), b) and/or c),
e) optional extraction of the collected wastewaters from step d) with toluene and recycling of the thus obtained organic phase into step a),
f) freeing the collected wastewaters from step d) or, if optional step e) is performed, the extracted wastewater from step e) of toluene in a toluene stripper to obtain a toluene-containing offgas stream,
g) supplying at least one offgas stream from steps a), b), c), d), e) or f) into an offgas condenser and removing the toluene present in the at least one offgas stream in this offgas condenser,
wherein the process comprises the further step of:
h) supplying the offgas stream generated in step g) after the condensing-out of the toluene to a thermal exhaust air purification, wherein nitrogen is added to the offgas stream to be supplied to the offgas condenser or to the offgas stream leaving the offgas condenser, wherein preferably a nitrogen concentration in the offgas stream of at least 0.1 vol % is established, particularly preferably of at least 0.5 vol %.

BACKGROUND

Dinitrotoluene (DNT) is an intermediate in the production of toluylene diisocyanate (TDI) which is an important precursor in the production of polyurethanes and is produced on a large industrial scale.

The production of dinitrotoluene by nitration of toluene with nitrating acid (mixture of nitric acid and sulfuric acid) has already been the subject of numerous publications and patent applications (Ullmanns Enzyklopedie der technischen Chemie, 4th edition, volume 17, page 391 ff, 1979, Verlag Chemie Weinheim/New York). As described for example in H. Hermann, J. Gebauer, P. Konieczny, "Industrial Nitration of Toluene to Dinitrotoluene" in ACS-Symposium, Series 623, 234-249, 1996, ed. L. F. Albright, R. V. C Carr, R. J. Schmitt, industrial production proceeds continuously in two stages in predominantly isothermal fashion with nitric acid in the presence of sulfuric acid as catalyst in such a way that a) the reaction mixture obtained in the dinitration (nitration of mononitrotoluene—MNT—to DNT) is separated by phase separation and the thus obtained spent acid is reconcentrated with nitric acid and then mixed with toluene and supplied to the mononitration (nitration of toluene to MNT) and
b) once reaction has been effected the reaction mixture from the mononitration is resolved in a separation stage into an organic phase comprising the mononitrotoluene and an aqueous phase comprising predominantly the sulfuric acid (spent acid) and
c) the mononitrotoluene-comprising organic phase obtained in b) is supplied to the dinitration and the mononitrotoluene is reacted there with nitric acid in the presence of sulfuric acid to afford dinitrotoluene.

To achieve commercial specifications the thus obtained crude DNT is typically processed in downstream stages, predominantly washes, and thus largely freed of dissolved sulfuric and nitric acid contents and also of secondary components formed in the reaction stages, for example mono-, di- and trinitrocresols (referred to hereinbelow simply as nitrocresols), picric acid and nitrobenzoic acids. Typical commercial DNT products have DNT contents >98.5 wt %, less than 0.1 wt % of mononitrotoluene, less than 0.1 wt % of trinitrotoluene and less than 0.1 wt % of other secondary components based on the weight of the DNT product mixtures with DNT yields of >98% and toluene conversions of >99.9%. Also significant is the weight ratio of the sum of the 2,4- and 2,6-DNT isomers to the sum of the 2,3-, 3,4-, 2,5- and 3,5-DNT isomers. According to commercial specifications the content of the sum of the 2,4- and 2,6-DNT isomers in the crude DNT is >95 wt % based on the weight of the crude DNT. It is preferable when the content of 2,4-DNT is 79.0-81.0 wt % based on the sum of the weights of 2,4-DNT and 2,6-DNT. Accordingly, the content of 2,6-DNT is 19.0-21.0 wt % based on the sum of the weights of 2,4-DNT and 2,6-DNT.

In addition to the crude DNT, in the resolution of the reaction mixture obtained in the mononitration, the process affords spent acid which leaves the system as a second mass flow. The spent acid typically has a sulfuric acid content of 70-80 wt % and typically comprises >0.1, preferably >0.2 to 3.0 wt % of unconverted nitric acid, nitrose from oxidation processes occurring in secondary reactions, >0.2 wt % of MNT not separated in the phase separation and typically water in a concentration range of >16 to <30 wt % (comprising water introduced with the sulfuric acid freshly employed in the process, water present in the nitric acid and water formed during the nitrations of the toluene and of the mononitrotoluene) in each case based on the weight of the spent acid.

EP 1 496 043 A1 describes a process for the workup of aqueous wastewaters generated during the nitration of toluene to dinitrotoluene with nitrating acid, wherein the acidic and alkaline wastewaters from the dinitrotoluene wash and the aqueous distillate from the sulfuric acid concentration are combined so that a pH of below 5 (measured at 70° C.) is established. The aqueous phase and organic phase formed are then separated by phase separation. The organic components present in the aqueous phase are extracted with toluene and the toluene phase enriched with organic components is then supplied to the nitration of toluene. The extraction described is a step distinct from the crude dinitrotoluene wash. The application further discloses that the aqueous phase from the extraction may be supplied to a steam stripping. The obtained water vapor-toluene mixture is condensed and the toluene present in the condensate may be recycled into the nitration after phase separation. The application does not disclose subjecting offgas streams from the gas spaces of the apparatuses employed in the nitration reaction, in the wash and/or in the DNT-water phase separation to a condensation to remove toluene.

The nitrogen oxides ($NO_x$) formed in the nitration may be treated with aqueous alkali metal hydroxide solution and washed out as sodium nitrate and nitrite as described in U.S. Pat. No. 5,313,009. In addition, carbon dioxide formed in the nitration process is bound as sodium carbonate.

U.S. Pat. No. 5,963,878 discloses a process wherein $NO_x$ gases are obtained from strategic regions of the nitration system, brought into contact with air and water, for example in a unit comprising a packed bed, at relatively high temperatures and under pressure, wherein the $NO_x$ gases are absorbed by the water to form weak nitric acid. The weak nitric acid is recycled into the reaction process. Carbon dioxide is not absorbed in a $NO_x$ gas scrubbing tower when the gas scrubbing tower is operated in an acidic mode. Clean $NO_x$-free vent gas is discharged as flue gas from the unit comprising a packed bed.

Common to all of the processes is that a further treatment of the offgases from nitration plants is not provided for.

EP1880989A1 describes that numerous past studies sought to improve the quality of the crude DNT and thus to increase the yield based on toluene and nitric acid. For all processes for producing DNT by nitration of toluene with nitric acid it is a prerequisite for economic running of the process that the spent acids generated during the process may be reprocessed in such a way that they may be reemployed as reaction medium in the reaction process (as described in EP 155 586 A and U.S. Pat. No. 5,275,701 A for example).

However, other significant factors affecting the choice of a DNT nitration process also include its inherent safety, the robustness with which it can be operated, the selectivity with and extent to which the toluene can be converted to dinitrotoluene, and the specific use of nitric acid necessary for the conversion of the toluene to dinitrotoluene. It is thanks to these developments that the current DNT processes have reached a level of maturity which allows all of them to produce DNT in high yields with a low content of byproducts.

However, it was found during operation of a nitration plant for producing dinitrotoluene from toluene that the isolated molar amount of dinitrotoluene end product and of the byproducts inherently associated with the process such as cresols and their degradation products and also mononitrotoluene and trinitrotoluene was lower than the corresponding amount of toluene employed. The outlet for this loss is evidently the production plant offgas which is undesirable from an ecological standpoint. The loss is also associated with economic disadvantages.

There was therefore a need to improve existing nitration technology to reduce environmental contamination with organics via the offgas. It was furthermore sought ideally to effect the reduction in the environmental contamination such that it is associated with economic advantages. It was sought in particular to send toluene entrained in the offgas for economic recovery.

SUMMARY

The object is achieved by a process for producing dinitrotoluene, comprising the steps of:
a) nitration of toluene with a mixture of nitric acid and sulfuric acid with subsequent separation of a sulfuric-acid-containing aqueous phase formed during the nitration to obtain a crude dinitrotoluene,
b) washing the crude dinitrotoluene in a water wash with neutral and/or alkaline washing water, wherein after separation of the washing water employed in the last wash a prepurified dinitrotoluene is obtained which comprises not only dinitrotoluene but also at least water and
c) separating the water from the prepurified dinitrotoluene,
d) collecting the wastewaters from steps a), b) and/or c),
e) optional extraction of the collected wastewaters from step d) with toluene and recycling of the thus obtained organic phase into step a),
f) freeing the collected wastewaters from step d) or, if optional step e) is performed, the extracted wastewater from step e) of toluene in a toluene stripper to obtain a toluene-containing offgas stream,
g) supplying at least one offgas stream from steps a), b), c), d), e) or f) into an offgas condenser and removing the toluene present in the at least one offgas stream in this offgas condenser, wherein the process comprises the further step of:
h) supplying the offgas stream generated in step g) after the condensing-out of the toluene to a thermal exhaust air purification, wherein nitrogen is added to the offgas stream to be supplied to the offgas condenser or to the offgas stream leaving the offgas condenser, wherein preferably a nitrogen concentration in the offgas stream of at least 0.1 vol % is established, particularly preferably of at least 0.5 vol %.

DETAILED DESCRIPTION

The present invention is based on the insight that supplying an offgas stream or a plurality of offgas streams from steps a), b), c), d), e) or f) and condensing out the organic gaseous constituents makes it possible not only to reduce the proportion of organic compounds in the offgas stream but rather that toluene makes up a large part of the compounds present therein and after the condensing-out and purification can be supplied to the process again or else incinerated. In accordance with the invention the term "offgas stream" is to be understood as meaning a gas stream which in one of steps according to the invention is discharged from the gas space above the liquid process product of the respective process step or which is generated as a gaseous process product. The nitration in step a) may for example take place in a reactor containing a liquid phase in which the chemical reaction takes place. There is a gas space above this liquid phase since the liquid phase does not completely fill the internal volume of the reactor. Liquid phases with gas spaces above them are likewise present in the respective apparatuses of steps b) (e.g. stirred washing containers), c) (e.g. phase separators) and d) (e.g. storage tanks). Step f) generates a toluene-laden stripping gas which is referred to as an offgas stream in accordance with the invention.

The removing of toluene in step g) is effected as completely as possible in accordance with the invention. It is preferable to establish a residual content of toluene in the offgas stream leaving the offgas condenser of not more than 10% of the toluene amount present in the offgas stream supplied to the offgas condenser.

The inventive procedure also ensures process and plant safety in the handling of nitrogen-oxide-containing toluene offgases. The process is preferably operated continuously.

The word "a" in the context of the present invention in connection with countable parameters should be understood as meaning the number "one" rather than merely the indefinite article only when this is stated explicitly (for instance by the expression "exactly one"). For example, the expression "a condenser" does not preclude the presence of a plurality of condensers (connected in series or parallel).

In the context of the present invention non-condensable gases are to be understood as meaning substances that are in gaseous form under standard conditions and cannot be liquefied with condensers customary in large-scale industry (temperatures down to −20° C.). Typical examples are nitrogen oxides ($NO_x$) and carbon dioxide.

The addition of nitrogen in step h) according to the invention has the effect that the mixture of nitrogen oxides and toluene present in the offgas stream is outside the concentration range for forming an explosive mixture at the temperature and pressure prevailing in the offgas stream. Preference is given to adding nitrogen to the offgas stream leaving the offgas condenser which is supplied to the thermal exhaust air purification since before condensation the offgas stream generally still comprises water which counters the formation of an explosive mixture. Nitrogen is preferably added to the offgas stream immediately after leaving the condenser.

In the process according to the invention it is preferable when in step g) the offgas stream from step f) is supplied to the offgas condenser, all offgas streams from steps a), b) and c) and also optionally d) and optionally e) being combined and fed either into the offgas stream from step f) that is to be supplied to the offgas condenser or—preferably—into the offgas stream leaving the offgas condenser.

The nitration of toluene may be performed for example in a manner known per se in a continuous, two-stage process, wherein in the first stage a crude mononitrotoluene is obtained which in the second stage is converted into the crude dinitrotoluene.

The washing of the crude dinitrotoluene may be effected in the sequence neutral washing water, then alkaline washing water and finally neutral washing water. The separation in step c) may be accomplished in a storage tank comprising a separator for example.

In a preferred embodiment of the process according to the invention an absolute pressure in the range from 10 mbar to 1200 mbar, preferably from 100 mbar to 1150 mbar, is established in the offgas condenser in step g). Independently thereof, a temperature of 20° C. to 75° C., preferably of 25° C. to 60° C. and particularly preferably of 30° C. to 45° C. may be established in the offgas condenser in step g). The offgas condenser employed may be a heat exchanger for example. The temperature of the offgas is preferably measured in the supply pipe immediately upstream of the offgas condenser. The temperature of the offgas after the condensation is for example 10° C. to 30° C., preferably 15° C. to 25° C.

Offgas condensers that may be employed in the context of the process according to the invention include for example condensers comprising a cooling coil or helical tube, double tube coolers or tube bundle heat exchangers. Suitable materials for construction of an exhaust air condenser are for example glass and metals such as steel, in particular corrosion-resistant alloyed steel or enamelled steel. Glass has the advantage that any deposits arising on the product side of the condenser may be easily spotted while steel provides more degrees of freedom in terms of pressure. The cooling medium used is preferably a cooling water stream of a suitable temperature. However, other heat transfer media such as heat transfer oils or organic solvents for example may likewise be employed. The mixture liquefied from the offgas stream in the exhaust air condenser consisting essentially of water, toluene and possibly dissolved nitrogen oxides is collected as discharge and sent for further processing.

In an advantageous configuration of the process according to the invention the toluene condensed out in step g) may be supplied to the nitration in step a). Before being supplied to the nitration the toluene may if desired be subjected to a purification. It is preferable when the toluene is recycled into the mononitration stage, preferably into the wastewater workup of the mononitration.

In the process according to the invention the offgas stream to be supplied to the offgas condenser or—preferably—the offgas stream leaving the offgas condenser can be freed of nitrogen oxides. The separation of nitrogen oxides is particularly preferably effected after the addition of nitrogen into the gas stream leaving the offgas condenser. The nitrogen oxide separation may be effected for example by using a $NO_x$ absorber, such as is described in U.S. Pat. No. 5,963,878, in particular in column 2, line 12 to column 3, line 27.

The offgas stream generated in step g) after the condensing-out of the toluene may subsequently be supplied to a thermal exhaust air purification, for example to an incinerator. The offgas stream can be combined with $NO_x$-containing offgases from the nitration process after passing through the offgas condenser before being supplied to the thermal exhaust air purification. Any nitrogen oxide separation is then effected after addition of these $NO_x$-containing offgases. Alternatively, as is known to one skilled in the art the offgas comprising nitrogen oxide may be passed into a thermal exhaust air purification suitable for the composition.

In the context of the process according to the invention it may further be provided that the sulfuric-acid-containing aqueous phase be purified and if desired concentrated and/or recycled after the separation.

In step d) of the process according to the invention the wastewaters from the nitration, the washing and/or the water separation from the pre-purified dinitrotoluene/the aqueous phase obtained in the optionally performed extraction, i.e. the wastewaters from steps a), b) and/or c), are collected. Since the wastewaters from the SAC sulfuric acid concentration may likewise comprise toluene it is possible also to combine these wastewaters with the remaining wastewaters in step d). The collected wastewaters from step d) or, if optional step e) is performed, of the extracted wastewater from step e) are subsequently freed of toluene in a toluene stripper by steam stripping (step f)). In a preferred configuration of the invention it is then only the moist offgases from the toluene stripper that are freed of toluene and water in a condenser, such as a tube bundle heat exchanger, (step g)). This essentially organics-free offgas is then supplied with nitrogen (step h)). This offgas stream is subsequently combined with the offgas streams from steps a), b) and c) and also optionally d) and optionally e) and preferably incinerated together with $NO_x$ gases generated in the process.

The invention is elucidated in detail hereinafter. Various embodiments may be combined with one another as desired, unless the opposite is apparent to the person skilled in the art from the context.

step a) of the process according to the invention may in principle be effected in accordance with any prior art processes for nitration of toluene. Preference is given to the reaction of toluene with a mixture of nitric acid and sulfuric acid with continuous, isothermal, two-stage running of the process such as is described in EP 1 880 989 A1 and documents cited therein, said subject-matter hereby being incorporated into the present disclosure. The purification and concentration (SAC) of the sulfuric acid generated for reuse in the nitration process may be performed by established prior art processes. One preferred process therefor is described in DE 196 36 191 B4, said subject-matter hereby being incorporated into the present disclosure. In particular the offgas streams generated upstream of the concentration stages are suitable for a procedure for obtaining and processing nitrogen oxides to afford nitric acid according to U.S. Pat. No. 5,963,878.

In step b) of the process according to the invention the individual washing steps may in principle be performed in any desired sequence. However preference is given to the sequence (1) neutral wash—(2) alkaline wash—(3) neutral wash. (The wastewater obtained in the first washing step after phase separation is acidic on account of its content of washed-out acid. This first wash is therefore occasionally also referred to as an "acidic wash"). However all other conceivable combinations are possible, as is a washing sequence without an alkaline wash. The thus generated wastewater streams from the neutral and the alkaline DNT wash and preferably also from the sulfuric acid concentration are preferably combined (step d)). After the merging of the recited streams separation of an organic phase takes place. This organic phase consists of MNT and DNT and also byproducts of the nitration, predominantly nitrocresols, picric acid and nitrobenzoic acids. To separate the organic phase formed, the combined wastewater streams are then passed into a suitable separation vessel. It is particularly preferable when step b) is effected according to the procedure described in EP 1 496 043 A1 which is hereby incorporated into the present disclosure. $NO_x$-containing exhaust air may be generated in the acidic and neutral media in the apparatuses of step b).

The purified moist DNT is intermediately stored in a storage tank, water settling out in step c) which is removed by means of a separator. This separated water is preferably combined with the previously mentioned aqueous streams in step d).

In the hitherto described process steps a) to d) gaseous offgas streams are generated which are discharged from the gas spaces above the liquid process product of the respective process step. If the respective process step a), b), c) or d) is performed in the absence of air, as is preferred for all of these steps in the process according to the invention, then the gas space comprises the respective inert gas employed for inertization (preferably nitrogen). Otherwise, the gas space comprises air. In all cases the gas space also comprises constituents of the respective liquid process product. This is because, from the liquid process products of the individual process steps, on account of limited gas solubility in the liquid phase, uncondensable gases outgas from this liquid phase into the gas space. In addition organic compounds are partially converted into the gas phase depending on the vapor pressure. The individual offgas streams comprise in varying compositions uncondensable gases (carbon monoxide, carbon dioxide, oxygen, nitrogen oxides, nitrogen), toluene, mononitrotoluene, dinitrotoluene and possibly water. Process offgases are preferably withdrawn from apparatuses in step a) concerned with nitration of toluene to dinitrotoluene, phase separation, sulfuric acid purification and concentration, from apparatuses and containers in step b), DNT washing and wastewater processing, and also from containers and tanks from step c), storage, and step d), wastewater collection, and supplied to the offgas condensation in step g) or preferably to the offgas stream leaving the offgas condensation. The purification of the offgas stream/of the offgas streams of nitrogen oxides may be effected in accordance with any processes known from the prior art. Employing a $NO_x$ absorber such as is described in U.S. Pat. No. 5,963,878, in particular in column 2, line 12 to column 3, line 27, is preferred. This nitrogen oxide separation is effected in a step g.1) that follows step g). This is particularly preferred in order to avoid the explosion limits of the toluene/oxygen offgas mixture that would arise upon introduction of oxygen into the offgas stream to the $NO_x$ absorption.

The optional extraction of the collected wastewaters from step e) with toluene is preferably effected as described in EP 1 496 043 A1.

In step g) of the process according to the invention the offgas stream is treated in an offgas condenser in order to recover entrained toluene.

The pressure in the offgas condenser employed in step g) is preferably chosen such that toluene and water may be optimally condensed out. The invention accordingly in particular also relates to a process where step g) is operated at an absolute pressure of 10 mbar to 1200 mbar, preferably from 100 mbar to 1150 mbar, particularly preferably from 100 mbar to 500 mbar. This pressure is preferably measured at the entrance to the offgas condenser (heat exchanger).

Preference is given to a process where in step g) in an offgas condenser operated as a heat exchanger the offgas is freed of toluene and partly of water by condensing-out and the org. phase is in turn freed of water and the organic condensate is supplied to a suitable workup, for example the wastewater workup in step b) or the mononitration of toluene in step a).

Suitable apparatuses are described for example in Reinhard Billet; "Verdampfung und ihre technischen Anwendungen"; Verlag Chemie Weinheim—Deerfield Beach, Fla.—Basel; 1981, chapter 4.1.2, pages 208 to 230.

A preferred embodiment for operating an offgas condenser is described hereinbelow:

The offgas from the toluene stripper from step f) is condensed in a heat exchanger and freed of toluene (step g)). The thus-treated offgas is then admixed with nitrogen and combined with the other non-toluene-containing offgases from the SAC, which is optionally freed of $NO_x$ by a process established in the literature, from the DNT reaction and from the DNT tanks and incinerated in a thermal exhaust air purification ("TAREX") (step h)).

The present invention is more particularly described hereinbelow with reference to working examples.

EXAMPLES

Example 1 (Comparative Example)

Untreated Offgas (No Toluene Condenser)

Moist, pure DNT is produced in accordance with steps a) to b) of the process according to the invention initially at a production capacity of 26 tons per hour and this is freed of water in a storage tank using a separator in step c). This affords pure, moist DNT. The 69 t/h of washing water remaining from step b) are passed into a stripping column and subjected to 3.5 t/h of 6 bar steam. The bottoms discharge from the stripping column consists of warm water and about 0.5 kg/h of toluene which are discharged to biological workup. The vapors at the top of the stripping column at atmospheric pressure comprise not only water but also 75 kg/h of toluene which are incinerated with the offgas.

Analysis of the offgas stream was by gas chromatography.

Example 2 (Comparative Example)

Recovery of Toluene from the Offgas without Addition of Nitrogen

Moist, pure DNT is produced in accordance with steps a) to b) of the process according to the invention initially at a production capacity of 26 tons per hour and this is freed of water in a storage tank using a separator in step c). This affords pure, moist DNT. The 69 t of washing water remaining from step b) having a temperature of 61° C. are passed into a stripping column and subjected to 3.5 t/h of 3.5 bar steam (steam stripping, step f)). The bottoms discharge from the stripping column consists of 69.4 t of water having a temperature of 67° C. which is discharged to biological workup. 3 t/h of vapors comprising 2.91 t of water and 81 kg/h of toluene are generated at a temperature of 65° C. at the top of the stripping column at a pressure of 250 mbar. These vapors are supplied to the offgas condensation in step g). In a first condenser 2.9 t/h of water and 1.9 kg/h of toluene are condensed. The remaining vaporous stream of 79.2 kg/h of toluene and 14 kg/h of water is then passed via a steam ejector into a second condensation stage at one bar of pressure to condense 75 kg/h of toluene and residual water at 19° C. The remaining gas stream comprising a residual toluene amount of 4 kg/h is incinerated in a thermal exhaust air purification.

Analysis of the offgas stream was by gas chromatography.

Example 3 (Inventive Example)

Recovery of Toluene from the Offgas and Safe Operation of the Offgas Lines

Moist, pure DNT is produced in accordance with steps a) to b) of the process according to the invention initially at a production capacity of 26 tons per hour and this is freed of water in a storage tank using a separator in step c). This affords pure, moist DNT. The 69 t of washing water remaining from step b) having a temperature of 61° C. are passed into a stripping column and subjected to 3.5 t/h of 3.5 bar steam (steam stripping, step f)). The bottoms discharge from the stripping column consists of 69.4 t of water having a temperature of 67° C. which is discharged to biological workup. 3 t/h of vapors comprising 2.91 t of water and 81 kg/h of toluene are generated at a temperature of 65° C. at the top of the stripping column at a pressure of 250 mbar. These vapors are supplied to the offgas condensation in step g). In a first condenser 2.9 t/h of water and 1.9 kg/h of toluene are condensed. The remaining vaporous stream of 79.2 kg/h of toluene and 14 kg/h of water is then passed via a steam ejector into a second condensation stage at one bar of pressure to condense 75 kg/h of toluene and residual water at 19° C. Immediately at the outlet from the second condensation stage an amount of nitrogen is metered into the offgas line to be supplied to the thermal offgas purification that is sufficient to establish, through this addition of nitrogen, a nitrogen concentration in the offgas stream of at least 0.6 vol % (step h)). The gas stream thus rendered nonexplosive comprising a residual toluene amount of 4 kg/h is incinerated in a thermal exhaust air purification, thus ensuring a particularly safe operation of the offgas line which connects the outlet from the second condensation stage with the thermal exhaust air purification. The offgas streams from steps a), b) and c) are combined and comprise <5 ppm of toluene. The combined offgas streams are fed into the offgas line which connects the second condensation stage with the thermal exhaust air purification immediately upstream of the thermal exhaust air purification.

Analysis of the offgas stream was by gas chromatography.

Example 4 (Inventive Example)

Further Utilization of the Toluene Obtained from the Offgas

The toluene/water mixture generated from example 3 in the second condensation stage which comprises 75 kg/h of toluene is run into a decanter. The organic phase is combined with fresh toluene and passed to the nitration and the aqueous phase is passed to the wastewater stripping column.

The invention claimed is:

1. A process for producing dinitrotoluene, comprising:
    a) nitrating toluene with a mixture of nitric acid and sulfuric acid with subsequent separation of a sulfuric-acid-containing aqueous phase formed during the nitration to obtain a crude dinitrotoluene,
    b) washing the crude dinitrotoluene in a water wash with neutral and/or alkaline washing water, wherein after separation of the washing water employed in the last wash a prepurified dinitrotoluene is obtained which comprises not only dinitrotoluene but also at least water,
    c) separating the water from the prepurified dinitrotoluene,
    d) collecting the wastewaters from steps a), b) and/or c),
    e) optional extraction of the collected wastewaters from step d) with toluene and recycling of the thus obtained organic phase into step a),
    f) freeing the collected wastewaters from step d) or, if optional step e) is performed, the extracted wastewater from step e) of toluene in a toluene stripper to obtain a toluene-containing offgas stream,
    g) supplying at least one offgas stream from steps a), b), c), d), a) or f) into an offgas condenser and removing the toluene present in the at least one offgas stream in this offgas condenser, and
    h) supplying the offgas stream generated in step g) after the condensing-out of the toluene to a thermal exhaust air purification, wherein nitrogen is added to the offgas stream to be supplied to the offgas condenser or to the offgas stream leaving the offgas condenser.

2. The process as claimed in claim 1, wherein in step g) the offgas stream from step f) is supplied to the offgas condenser and all offgas streams from steps a), b) and C) and also optionally d) and optionally e) are combined and fed either into the offgas stream from step g) that is to be supplied to the offgas condenser or into the offgas stream leaving the offgas condenser.

3. The process of claim 1, wherein the nitration of toluene in step a) is performed in a continuous, two-stage process, wherein in the first stage a crude mononitrotoluene is obtained which in the second stage is converted into the crude dinitrotoluene.

4. The process of claim 1, wherein the washing of the crude dinitrotoluene in step b) is effected such that initially neutral, then alkaline and finally neutral washing water is employed.

5. The process of claim 1, wherein the separation in step c) is accomplished in a storage tank comprising a separator.

6. The process of claim 1, wherein an absolute pressure in the range from 10 mbar to 1200 mbar, is established in the offgas condenser in step g).

7. The process of claim 1, wherein a temperature of 20° C. to 75° C. is established in the offgas condenser in step g).

8. The process of claim 1, wherein the toluene condensed out in step g) is supplied to the nitration in step a).

9. The process of claim 1, wherein the offgas stream to be supplied to the offgas condenser or the offgas stream leaving the offgas condenser is freed of nitrogen oxides.

10. The process of claim 1, wherein after the separation in step a) the sulfuric-acid-containing aqueous phase is purified and optionally concentrated and/or recycled.

11. The process of claim 1, wherein a nitrogen concentration in the offgas stream of at least 0.1 vol % is established.

12. The process of claim 11, wherein the nitrogen concentration in the offgas stream is at least 0.5 vol %.

13. The process of claim 6, wherein the absolute pressure is in the range of 100 mbar to 1150 mbar.

14. The process of claim 7, wherein the temperature is 25° C. to 60° C.

15. The process of claim 14, wherein the temperature is 30° C. to 45° C.

* * * * *